(12) United States Patent
Feld et al.

(10) Patent No.: US 9,179,936 B2
(45) Date of Patent: Nov. 10, 2015

(54) CONSTRAINING STRUCTURE WITH NON-LINEAR AXIAL STRUTS

(71) Applicant: Quattro Vascular PE Ltd., SGX Centre (SG)

(72) Inventors: Tanhum Feld, Moshav Merhavya (IL); Eitan Konstantino, Orinda, CA (US)

(73) Assignee: Quattro Vascular Pte Ltd., Singapore (SG)

( * ) Notice: Subject to any disclaimer, the term of this patent is extended or adjusted under 35 U.S.C. 154(b) by 93 days.

(21) Appl. No.: 13/761,525

(22) Filed: Feb. 7, 2013

(65) Prior Publication Data
US 2013/0218181 A1 Aug. 22, 2013

Related U.S. Application Data

(60) Provisional application No. 61/596,618, filed on Feb. 8, 2012.

(51) Int. Cl.
*A61B 17/50* (2006.01)
*A61B 17/3207* (2006.01)
(Continued)

(52) U.S. Cl.
CPC .......... *A61B 17/50* (2013.01); *A61B 17/320725* (2013.01); *A61M 25/104* (2013.01); *A61M 2025/1084* (2013.01)

(58) Field of Classification Search
CPC ............. A61M 2025/1084; A61M 2025/1086; A61M 2025/1045; A61M 25/104; A61B 17/320725; A61B 17/50; A61F 2/95; A61F 2/958; A61F 2/82; A61F 2/86; A61F 2/89; A61F 2/915; A61F 2/2433; A61F 2002/9505; A61F 2002/9511; A61F 2002/9665; A61F 2002/821; A61F 2002/823; A61F 2002/825; A61F 2002/828; A61F 2002/8483; A61F 2002/8486; A61F 2002/91508; A61F 2002/91516; A61F 2002/91525; A61F 2002/91533; A61F 2002/91541; A61F 2002/9155; A61F 2002/91558; A61F 2002/91575; A61F 2002/91583
USPC .............. 623/1.11, 1.12, 1.23, 2.11; 606/108, 606/191–200, 159; 604/96.01, 103, 103.03, 604/103.05, 103.06, 103.07, 103.08, 103.09
See application file for complete search history.

(56) References Cited

U.S. PATENT DOCUMENTS 2,701,559 A 2/1955 Cooper
2,854,983 A 10/1958 Baskin
(Continued)

FOREIGN PATENT DOCUMENTS

CN 1568165 A 1/2005
EP 0 565 796 10/1993
(Continued)

OTHER PUBLICATIONS

International Search Report and Written Opinion dated Apr. 19, 2013 in Application No. PCT/US13/25032, filed Feb. 7, 2013.
(Continued)

*Primary Examiner* — Katrina Stransky
*Assistant Examiner* — Katherine Schwiker
(74) *Attorney, Agent, or Firm* — Knobbe Martens Olson & Bear LLP

(57) ABSTRACT

A constraining structure for use with a balloon catheter can include multiple longitudinal struts and multiple, sinusoidal shaped radial rings. The constraining structure can expand to form a pattern of channels including substantially square windows. The constraining structure can modify, restrict, and control a shape and/or size of the balloon when inflated. Inflating the balloon catheter within the constraining structure can provide nonuniform pressure on a vessel wall adjacent the balloon.

12 Claims, 2 Drawing Sheets

(51) Int. Cl.
*A61M 25/10* (2013.01)
*A61F 2/06* (2013.01)

(56) References Cited

U.S. PATENT DOCUMENTS

| | | | |
|---|---|---|---|
| 3,045,677 A | 7/1962 | Wallace | |
| 3,467,101 A | 9/1969 | Fogarty et al. | |
| 3,825,013 A | 7/1974 | Craven | |
| 4,327,736 A | 5/1982 | Inoue | |
| 4,456,011 A | 6/1984 | Warnecke | |
| 4,483,340 A | 11/1984 | Fogarty et al. | |
| 4,637,396 A | 1/1987 | Cook | |
| 4,723,549 A | 2/1988 | Wholey et al. | |
| 4,796,629 A | 1/1989 | Grayzel | |
| 4,921,484 A | 5/1990 | Hillstead | |
| 4,976,711 A | 12/1990 | Parins et al. | |
| 4,998,539 A | 3/1991 | Delsanti | |
| 5,071,407 A | 12/1991 | Porter et al. | |
| 5,100,386 A | 3/1992 | Inoue | |
| 5,133,732 A | 7/1992 | Wilkor | |
| 5,176,693 A | 1/1993 | Pannek | |
| 5,181,911 A | 1/1993 | Shturman | |
| 5,190,058 A | 3/1993 | Jones et al. | |
| 5,196,024 A | 3/1993 | Barath | |
| 5,222,971 A | 6/1993 | Willard et al. | |
| 5,224,945 A | 7/1993 | Pannek, Jr. | |
| 5,263,963 A | 11/1993 | Garrison et al. | |
| 5,308,356 A | 5/1994 | Blackshear et al. | |
| 5,320,634 A | 6/1994 | Vigil et al. | |
| 5,336,178 A | 8/1994 | Kaplan | |
| 5,336,234 A | 8/1994 | Vigil et al. | |
| 5,344,419 A | 9/1994 | Spears | |
| 5,449,372 A | 9/1995 | Schmaltz et al. | |
| 5,456,666 A | 10/1995 | Campbell et al. | |
| 5,456,667 A | 10/1995 | Ham et al. | |
| 5,460,607 A | 10/1995 | Miyata et al. | |
| 5,501,694 A | 3/1996 | Ressemann et al. | |
| 5,527,282 A | 6/1996 | Segal | |
| 5,556,408 A | 9/1996 | Farhat | |
| 5,562,620 A | 10/1996 | Klein et al. | |
| 5,571,086 A | 11/1996 | Kaplan et al. | |
| 5,607,442 A | 3/1997 | Fischell et al. | |
| 5,609,574 A | 3/1997 | Kaplan et al. | |
| 5,616,149 A | 4/1997 | Barath | |
| 5,620,457 A | 4/1997 | Pinchasik et al. | |
| 5,628,746 A | 5/1997 | Clayman | |
| 5,628,755 A | 5/1997 | Heller et al. | |
| 5,643,210 A | 7/1997 | Iacob | |
| 5,695,469 A | 12/1997 | Segal | |
| 5,702,410 A | 12/1997 | Klunder et al. | |
| 5,713,863 A | 2/1998 | Vigil et al. | |
| 5,730,698 A | 3/1998 | Fischell et al. | |
| 5,733,303 A | 3/1998 | Israel et al. | |
| 5,735,816 A | 4/1998 | Lieber et al. | |
| 5,755,781 A | 5/1998 | Jayaraman | |
| 5,772,681 A | 6/1998 | Leoni | |
| 5,776,181 A | 7/1998 | Lee et al. | |
| 5,797,935 A | 8/1998 | Barath | |
| 5,810,767 A | 9/1998 | Klein | |
| 5,827,321 A | 10/1998 | Roubin et al. | |
| 5,863,284 A | 1/1999 | Kleiin | |
| 5,868,708 A | 2/1999 | Hart et al. | |
| 5,868,719 A | 2/1999 | Tsukernik | |
| 5,868,779 A | 2/1999 | Ruiz | |
| 5,868,783 A | 2/1999 | Tower | |
| 5,869,284 A | 2/1999 | Cao et al. | |
| 5,904,679 A | 5/1999 | Clayman | |
| 5,906,639 A | 5/1999 | Rudnick et al. | |
| 5,919,200 A | 7/1999 | Stambaugh et al. | |
| 5,961,490 A | 10/1999 | Adams | |
| 5,967,984 A | 10/1999 | Chu et al. | |
| 5,987,661 A | 11/1999 | Peterson | |
| 6,013,055 A | 1/2000 | Bampos et al. | |
| 6,036,689 A | 3/2000 | Tu et al. | |
| 6,036,708 A | 3/2000 | Sciver | |
| 6,053,913 A | 4/2000 | Tu et al. | |
| 6,059,811 A | 5/2000 | Pinchasik et al. | |
| 6,077,298 A | 6/2000 | Tu et al. | |
| 6,102,904 A | 8/2000 | Vigil et al. | |
| 6,106,548 A | 8/2000 | Roubin et al. | |
| 6,129,706 A | 10/2000 | Janacek | |
| 6,156,265 A | 12/2000 | Sugimoto | |
| 6,190,403 B1 | 2/2001 | Fischell et al. | |
| 6,206,910 B1 | 3/2001 | Berry et al. | |
| 6,217,608 B1 | 4/2001 | Penn et al. | |
| 6,235,043 B1 | 5/2001 | Reiley et al. | |
| 6,241,762 B1 | 6/2001 | Shanley | |
| 6,245,040 B1* | 6/2001 | Inderbitzen et al. | 604/103.07 |
| 6,261,319 B1 | 7/2001 | Kveen et al. | |
| 6,309,414 B1 | 10/2001 | Rolando et al. | |
| 6,319,251 B1 | 11/2001 | Tu et al. | |
| 6,361,545 B1 | 3/2002 | Macoviak et al. | |
| 6,416,539 B1 | 7/2002 | Hassdenteufel | |
| 6,454,775 B1 | 9/2002 | Demarais et al. | |
| 6,540,722 B1 | 4/2003 | Boyle et al. | |
| 6,605,107 B1 | 8/2003 | Klein | |
| 6,616,678 B2 | 9/2003 | Nishtala et al. | |
| 6,626,861 B1 | 9/2003 | Hart et al. | |
| 6,652,548 B2 | 11/2003 | Evans et al. | |
| 6,656,351 B2 | 12/2003 | Boyle | |
| 6,695,813 B1 | 2/2004 | Boyle et al. | |
| 6,939,320 B2 | 9/2005 | Lennox | |
| 6,942,680 B2 | 9/2005 | Grayzel et al. | |
| 7,186,237 B2 | 3/2007 | Meyer et al. | |
| 7,357,813 B2 | 4/2008 | Burgermeister | |
| 7,686,824 B2 | 3/2010 | Konstantino et al. | |
| 7,691,119 B2 | 4/2010 | Farnan | |
| 7,708,748 B2 | 5/2010 | Weisenburgh, II et al. | |
| 7,931,663 B2 | 4/2011 | Farnan et al. | |
| 8,388,573 B1 | 3/2013 | Cox | |
| 2003/0023200 A1 | 1/2003 | Barbut et al. | |
| 2003/0040790 A1* | 2/2003 | Furst | 623/1.11 |
| 2003/0078606 A1 | 4/2003 | Lafontaine et al. | |
| 2003/0114915 A1* | 6/2003 | Mareiro et al. | 623/1.11 |
| 2003/0153870 A1 | 8/2003 | Meyer et al. | |
| 2003/0195609 A1 | 10/2003 | Berenstein et al. | |
| 2004/0034384 A1 | 2/2004 | Fukaya | |
| 2004/0143287 A1* | 7/2004 | Konstantino et al. | 606/194 |
| 2004/0210299 A1 | 10/2004 | Rogers et al. | |
| 2004/0230293 A1 | 11/2004 | Yip et al. | |
| 2005/0271844 A1 | 12/2005 | Mapes et al. | |
| 2006/0015133 A1* | 1/2006 | Grayzel et al. | 606/192 |
| 2006/0085025 A1 | 4/2006 | Farnan et al. | |
| 2006/0271093 A1 | 11/2006 | Holman et al. | |
| 2007/0073376 A1 | 3/2007 | Krolik et al. | |
| 2009/0105686 A1 | 4/2009 | Snow et al. | |
| 2009/0227949 A1 | 9/2009 | Knapp et al. | |
| 2010/0042121 A1 | 2/2010 | Schnieder et al. | |
| 2011/0071616 A1 | 3/2011 | Clarke et al. | |
| 2012/0059401 A1* | 3/2012 | Konstantino et al. | 606/159 |
| 2012/0245607 A1* | 9/2012 | Gershony et al. | 606/159 |
| 2013/0116655 A1* | 5/2013 | Bacino et al. | 604/509 |
| 2013/0211381 A1* | 8/2013 | Feld | 604/509 |
| 2013/0218181 A1 | 8/2013 | Feld et al. | |
| 2014/0066960 A1 | 3/2014 | Feld et al. | |

FOREIGN PATENT DOCUMENTS

| | | |
|---|---|---|
| EP | 0 623 315 | 11/1994 |
| EP | 0 832 608 | 4/1998 |
| EP | 1 042 997 | 10/2000 |
| WO | WO 98/05377 | 2/1998 |
| WO | WO 98/50101 | 11/1998 |
| WO | WO 2011/112863 | 9/2011 |
| WO | WO 2013/114201 | 8/2013 |
| WO | WO 2013/119735 | 8/2013 |

OTHER PUBLICATIONS

International Search Report for Application No. PCT/US2011/027982 mailed May 6, 2011.
International Search Report and Written Opinion in Application No. PCT/IB13/00217, mailed Jun. 14, 2013.

(56) References Cited

OTHER PUBLICATIONS

International Search Report and Written Opinion in Application No. PCT/US13/25032, mailed Apr. 19, 2013.

Supplemental Search Report for Application No. EP11754114 mailed Oct. 28, 2013.

* cited by examiner

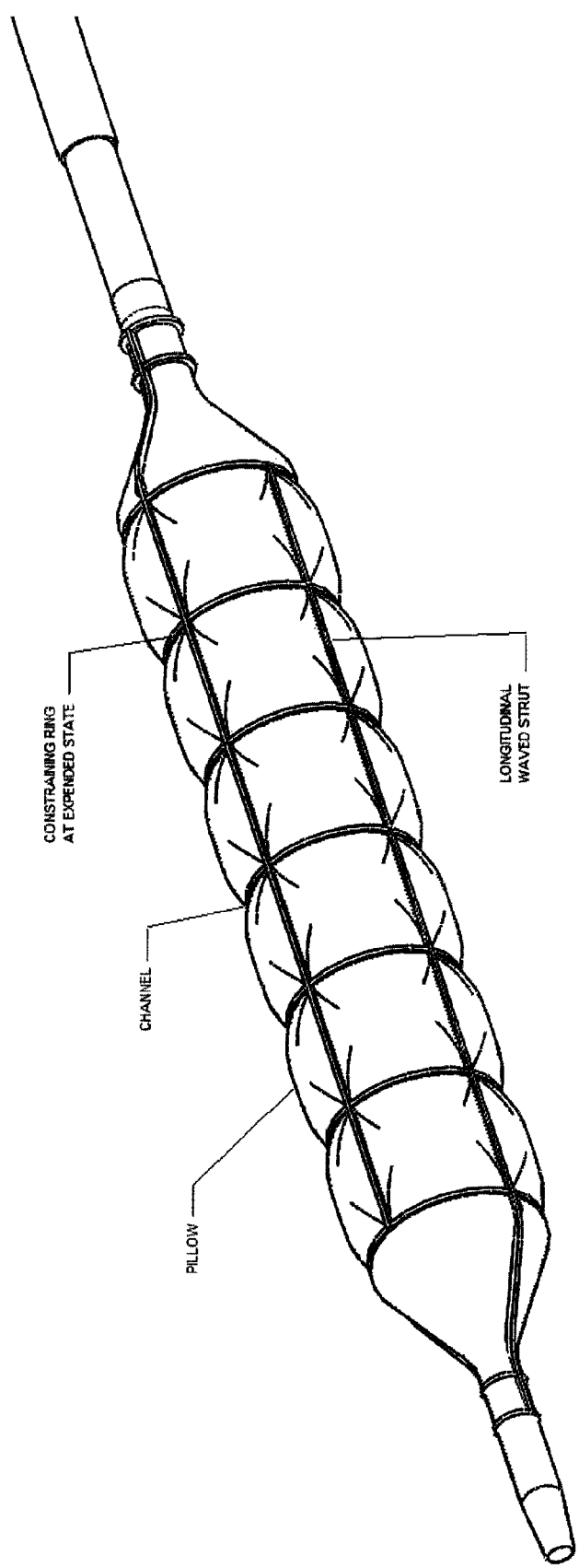

CONSTRAINING STRUCTURE WITH NON-LINEAR AXIAL STRUTS

This application claims the benefit of U.S. Provisional Application No. 61/596,618, filed Feb. 8, 2012, the entirety of which is incorporated by reference herein.

BACKGROUND OF THE INVENTION

Field of the Invention

The present invention is a balloon catheter for angioplasty procedures, comprising an elastic constraining structure mounted over the balloon where the structure has a mechanism of expansion to control the balloon inflation.

Conventional angioplasty balloons expand in an artery lesion at the least resistant areas of the lesion causing "dog bone" effect at the lesion ends and overexpansion in the softer areas, resulting in trauma to the vessel wall. Conventional angioplasty is associated with vessel displacement and its main mechanism of action is plaque compression where the vessel is significantly displaced or "pushed out" before reaction force can be generated and plaque compression takes place. During this process the balloon may expand in the axial direction (in addition to radial), a phenomenon that accelerates propagation of "cracks" in the vessel wall (dissections). This elongation continues after the balloon engages the lesion and the vessel wall and cause longitudinal stretch This mechanism of action causes a high rate of failure due to the vessel trauma (randomize studies in legs arteries document up to 40% acute failure rate and poor long term results with 20%-40% patency in one year). Attempts to modify the mechanism of action were mainly aimed at increasing the local force by adding cutting blades, wires or scoring elements that can penetrate into the vessel wall and create pre defined dissection plans. Those devices are used when encountering resistant lesions otherwise hard to crack open with conventional balloons. None of those technologies was designed to provide an alternative mechanism that leads to a gentler dilatation by minimizing vessel displacement and reducing the radial forces during balloon dilatation.

SUMMARY OF THE INVENTION

According to the present invention, a device that modifies the properties of an angioplasty balloon in order to provide uniform inflation and extraction of longitudinal forces in order to facilitate plaque extrusion and minimize vessel trauma. In the device presented herein, a novel constraining structure prevents non-cylindrical expansion using constraining rings that are spaced apart along the balloon working length leading to creation of small balloon segments (pillows) separates by grooves that facilitate plaque extrusion. The constraining structure also prevents longitudinal elongation of the balloon since it has a structure that shortens during expansion and constrains the balloon in both longitudinal and radial directions.

Computer simulation shows a decrease in radial forces using a balloon with the constraining structure. The constraining structure causes reduction in the rate of vessel dissections and perforations thru formation of an array of balloon pillows that provide gentle contact with the vessel wall and thru the formation of channels between these pillows that allow plaque flow and strain relief areas in the vessel wall.

Conventional balloon angioplasty does not provide strain relief to the vessel wall and suffer from high rate of dissections.

Other devices, such as cutting balloons and scoring devices (for example U.S. Pat. No. 7,691,119 Farnan) made to address resistant lesions by adding elements that can cut or score into the vessel wall and significantly, increase the local force ("focus force angioplasty"), but do not provide strain relief and gentle contact with the vessel wall. On the contrary, these devices include aggressive metallic components that are made to break hard plaque and mark their metal footprint on the vessel wall.

The constraining structure of the present invention takes advantage of the fact that by forcing the balloon into pillows topography the excessive length of the balloon is directed into a three dimensional shape and the surface area of the balloon increases. This mechanism shortens the overall balloon length during inflation and minimized longitudinal vessel stretch. Other devices such as stents or scoring cages that have structures over a balloon are using the balloon as an "activator" or expandable shell designed to increase the diameter of the stent or scoring stent and allow the balloon to inflate in full both radially and longitudinally and are therefore designed to expand as big as the inflated balloon, while the design present herein is made smaller than the inflated balloon, specifically aimed to modify, restrict and control the balloon inflated shape and size.

The combination of the advantages of the device described herein result in controlled non aggressive and predictable lesion dilation that addresses a major health concern.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows a scheme of the inflated device with circumferential and longitudinal pattern of channels and pillows.

DETAILED DESCRIPTION OF THE PREFERRED EMBODIMENT

Figure 1:
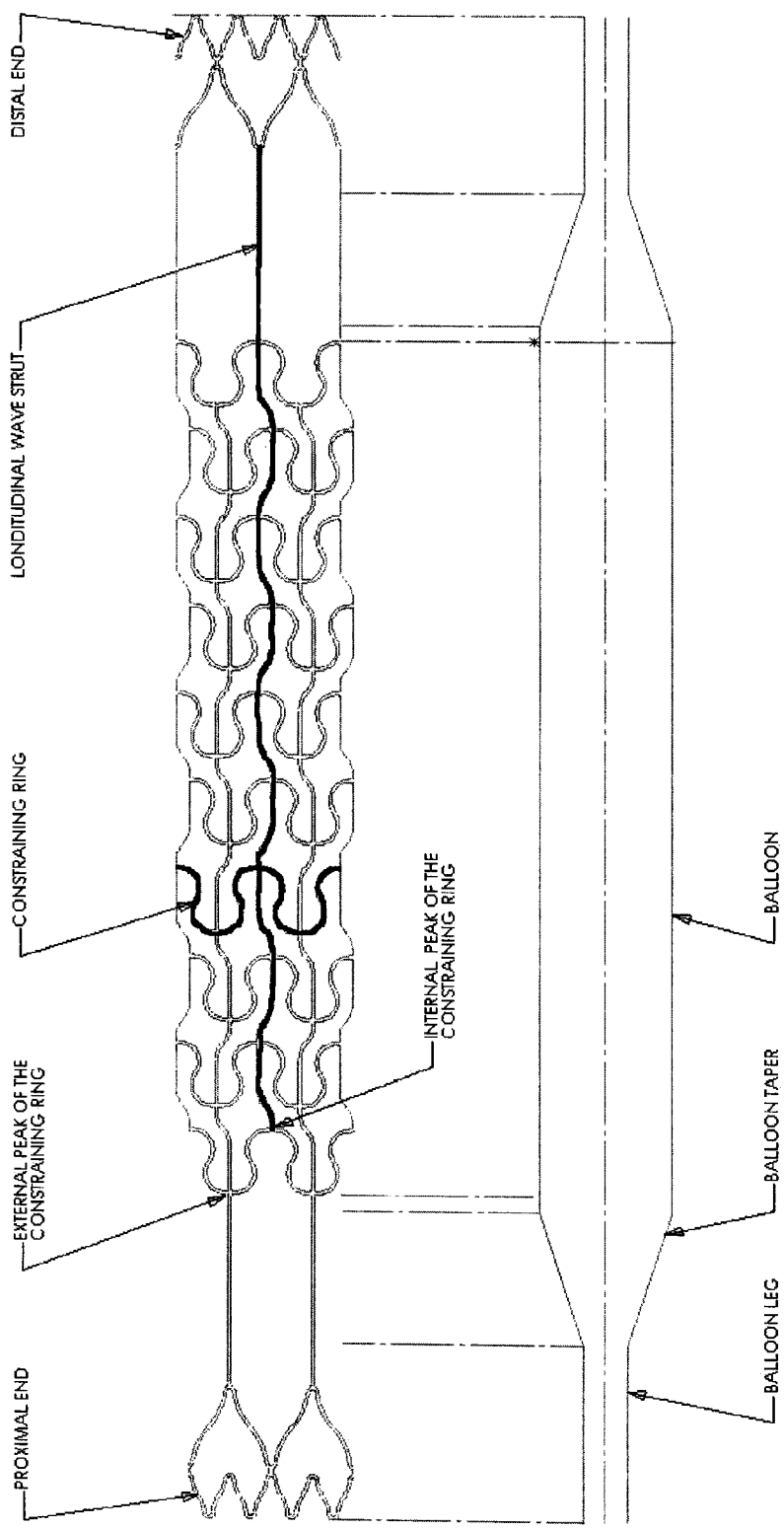
FIG. 1 show the layout of the constraining structure design adjacent to the balloon scheme, where the distal and proximal ends of the constraining structure are placed over the balloon legs, the constraining rings are spaced apart along the balloon length over the working length of the balloon, and an array of longitudinal waved struts interconnect between the constraining rings and the ends.

A balloon catheter comprising a catheter shaft and an inflatable balloon at its distal end and an elastic constraining structure is mounted over the balloon. The constraining structure is made from an elastic material such as Nitinol, elastic polymers or high strength fibers or mesh.

The device natural configuration is collapsed. Unlike "self-expanding stents," it is not "self-expanding" but to the contrary "self-closing" prior to expansion the constraining structure is tightly closed on the folded balloon. When the balloon is inflated the constraining structure is expanded by the balloon force up to a diameter smaller than the free inflated diameter of the balloon. The structure will self compress back to a small diameter when the balloon is deflated. Typically the distal end and a proximal end of the constraining structure are fixedly attached to the catheter at both sides of the balloon to prevent it from disengaging with the catheter. Attachment is made by means of adhesive or thermal bonding or other method known in the art.

The constraining structure comprises an array of sinusoidal constraining rings spaced apart along the balloon working length. Each ring has a sinus curve length defined by the length of the ring when fully straitened. For each ring the sinus curve length is smaller than the balloon expanded circumference. When expanded the rings expand to its maximal expansion resulting in a substantially circular ring shape that is smaller in diameter than the balloon diameter and force a substantially circular channel around the balloon outer surface.

Expansion of the constraining rings results in an array of channels along the balloon length and also results in shortening of the balloon. It is easier to understand the shortening caused by the rings as it is obvious that if the rings were removed from an inflated balloon the balloon would elongate.

The maximum expanded diameter of the constraining structure is mainly controlled by the length of the sinus curve rings. The maximum expanded diameter could be 0.15 mm-0.3 mm smaller than the balloon free inflated diameter but it could also be in the range of 0.1 mm to 0.5 mm or exceed this range depending on the material of choice and the specifics of the design. For example for 3 mm balloon the maximum expanded diameter of the structure made of nitinol is in the range of 2.6 mm-2.85 mm. If the maximum expanded diameter is out of the desirable range the device will fail to perform. For example, if the maximum expanded diameter is similar or larger than the balloon free expanded diameter, the constraining structure would not be able to restrict the free expansion of the balloon and pillows will not form. If the structure is too small, the forces applied by the balloon would cause the structure to break and the device will fail, risking patient's safety.

The constraining rings are interconnected by a circumferential array of interlacing longitudinal waved struts. The number of struts is usually twice the number of the sine waves in the constraining ring. For example the structure scheme shows a two waves sine ring and therefore four longitudinal waved struts. Each strut begins near one end of the constraining structure and ends at the last constraining ring near the opposite end. It does not continue all the way to the opposite end in order to allow proper functionality and expansion. The following strut begins near the opposite end of the constraining structure and ends at the last constraining rings near the first end of the balloon, such that the opposing ends are not interconnected by the longitudinal waved struts.

This construction result in the last ring being connected to the ends with half the number of struts only. If the struts were to continue all the way to the opposing end it would restrict the first ring from expanding homogeneously over the balloon as the intermediate rings expand.

The struts connect to the first constraining rings at the external peaks of the ring and thus forming a structure that shortens when expanded. If the struts were connected to the first constraining rings at the internal peaks of the ring than the structure would elongate when expanded.

It is particularly important not to have "spine" or struts that are connected to both proximal and distal end of the balloon. The current structure in FIG. 1 in which two (or more) longitudinal struts are connected to the distal end of the balloon and two (or more) other interlacing struts connected to the proximal end of the balloon create "push/pull" forces during inflation and longitudinal struts are moving in opposing directions during inflation in order to apply compressive forces on the balloon and allow it to shorten. This "tilt" function supports expansion of the pillows at lower pressure. The longitudinal waved struts form longitudinal channels over the balloon outer surface and together with the circular channels formed by the rings it results in substantially square pattern of channels ("windows") and balloon pillows protruding in the windows.

What is claimed is:

1. A balloon catheter, comprising
a catheter body;
a constraining structure comprising:
    a plurality of expandable, radial rings spaced apart along a length of the constraining structure, said plurality of radial rings comprising a proximal end ring and a distal end ring;
    a plurality of longitudinal struts spaced along a circumference of the constraining structure, the plurality of longitudinal struts comprising a first longitudinal strut and a second longitudinal strut, a first end of the first longitudinal strut attached to the catheter body and a second end of the first longitudinal strut attached to said proximal end ring, a first end of the second longitudinal strut attached to the catheter body and a second end of the second longitudinal strut attached to said distal end ring,
    wherein the constraining structure is configured to be positioned over the balloon catheter and wherein the constraining structure has an expanded and a collapsed state and is biased to be in the collapsed state, and
wherein the first longitudinal strut moves in a first axial direction and the second longitudinal strut moves in a second axial direction during expansion of the constraining structure, the second axial direction being opposite the first axial direction.

2. The balloon catheter of claim 1, wherein the radial rings comprise one or more first peaks extending towards a proximal end of the constraining structure and one or more second peaks extending towards a distal end of the constraining structure.

3. The balloon catheter of claim 1, wherein each longitudinal strut is attached to a peak of the radial ring closest to its point of attachment to the catheter body.

4. The balloon catheter of claim 1, wherein the radial rings comprise one or more sine waves.

5. The balloon catheter of claim 4, wherein the number of struts is twice a number of longitudinal sine waves in the radial rings.

6. The balloon catheter of claim 1, wherein the longitudinal struts are waved struts.

7. The balloon catheter of claim 1, wherein the first longitudinal strut is attached to the catheter body by a distal end of the constraining structure, and wherein the second longitudinal strut is attached to the catheter body by a proximal end of the constraining structure.

8. A method of expanding a balloon catheter in a vessel of a patient, the method comprising:
    positioning the balloon catheter so that a balloon of the balloon catheter is adjacent a treatment site in a vessel of a patient, the balloon catheter comprising a catheter body and a constraining structure positioned over the balloon, the constraining structure comprising a plurality of longitudinal struts connecting a plurality of radial sinusoidal rings, the plurality of rings comprising a proximal end ring and a distal end ring, the plurality of longitudinal struts comprising a first longitudinal strut and a second longitudinal strut, a first end of the first longitudinal strut attached to the catheter body and a second end of the first longitudinal strut attached to the proximal end ring, a first end of the second longitudinal strut attached to the catheter body and a second end of the second longitudinal strut attached to said distal end ring, the constraining structure biased to be in a collapsed state; and inflating the balloon, thereby expanding the constraining structure and providing nonuniform pressure on a wall of the vessel adjacent the balloon, the first longitudinal strut moving in a first axial direction and the second longitudinal strut moving in a second axial direction during expansion of the constraining structure, the second axial direction being opposite the first axial direction.

9. The method of claim 8, wherein inflating the balloon and expanding the constraining structure produces a pattern of channels comprising a pattern of substantially square windows in the constraining structure.

10. The method of claim 9, wherein inflating the balloon and expanding the constraining structure causes balloon pillows to protrude through said substantially square windows.

11. The method of claim 8, wherein expanding the constraining structure comprises expanding the constraining structure in a radial direction.

12. The method of claim 8, wherein expanding the constraining structure comprises at least one of modifying, restricting, and controlling a shape and/or size of the balloon when inflated.

\* \* \* \* \*

UNITED STATES PATENT AND TRADEMARK OFFICE
CERTIFICATE OF CORRECTION

PATENT NO.       : 9,179,936 B2
APPLICATION NO.  : 13/761525
DATED            : November 10, 2015
INVENTOR(S)      : Tanhum Feld It is certified that error appears in the above-identified patent and that said Letters Patent is hereby corrected as shown below:

In the Specification

In column 2 at line 62, Change "not"self-expanding"" to --not "self-expanding"--.

In the Claims

In column 4 at line 48, In Claim 5, after "number of" insert --longitudinal--.

In column 4 at line 49, In Claim 5, change "a" to --the--.

In column 4 at line 49, In Claim 5, after "number of" delete "longitudinal".

Signed and Sealed this
Seventh Day of June, 2016

Michelle K. Lee
*Director of the United States Patent and Trademark Office*